(12) United States Patent
Lancaster et al.

(10) Patent No.: US 9,809,858 B2
(45) Date of Patent: Nov. 7, 2017

(54) O-GLYCAN PATHWAY OVARIAN CANCER SIGNATURE

(71) Applicant: H. LEE MOFFITT CANCER CENTER AND RESEARCH INSTITUTE, INC., Tampa, FL (US)

(72) Inventors: Johnathan M. Lancaster, Tampa, FL (US); Douglas C. Marchion, Seminole, FL (US); Yin Xiong, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 120 days.

(21) Appl. No.: 14/387,321

(22) PCT Filed: Apr. 5, 2013

(86) PCT No.: PCT/US2013/035470
§ 371 (c)(1),
(2) Date: Sep. 23, 2014

(87) PCT Pub. No.: WO2013/152301
PCT Pub. Date: Oct. 10, 2013

(65) Prior Publication Data
US 2015/0080249 A1    Mar. 19, 2015

Related U.S. Application Data

(60) Provisional application No. 61/620,757, filed on Apr. 5, 2012.

(51) Int. Cl.
C12Q 1/68 (2006.01)
G01N 33/574 (2006.01)

(52) U.S. Cl.
CPC ..... C12Q 1/6886 (2013.01); G01N 33/57449 (2013.01); *C12Q 2600/106* (2013.01); *C12Q 2600/118* (2013.01); *C12Q 2600/158* (2013.01); *G01N 2800/52* (2013.01)

(58) Field of Classification Search
CPC ............ C12Q 1/6886; C12Q 2600/106; C12Q 2600/158; C12Q 2600/118; G01N 33/57449; G01N 2800/52
See application file for complete search history.

(56) References Cited

U.S. PATENT DOCUMENTS

| | | | |
|---|---|---|---|
| 2006/0019256 A1 | 1/2006 | Clarke et al. | |
| 2009/0275608 A1* | 11/2009 | Ossovskaya | C12Q 1/6886 514/307 |
| 2011/0306049 A1* | 12/2011 | Yamashita | C07K 16/40 435/6.12 |

OTHER PUBLICATIONS

"Altered mRNA expressions of sialyltransferases in ovarian cancers," by Wang et al., Gynecologic Oncology, vol. 99, No. 3, pp. 631-639.*

(Continued)

*Primary Examiner* — Reza Ghafoorian
(74) *Attorney, Agent, or Firm* — Meunier Carlin & Curfman LLC

(57) ABSTRACT

Biomarkers, methods, assays, and kits are provided for determining the prognosis of and treating a patient with ovarian cancer. Also disclosed are biomarkers, methods, assays, and kits for predicting the sensitivity of ovarian cancer cells to chemotherapy.

9 Claims, 3 Drawing Sheets

(56) References Cited

OTHER PUBLICATIONS

Bolstad BM, Irizarry RA, Astrand M, Speed TP. A comparison of normalization methods for high density oligonucleotide array data based on variance and bias. Bioinformatics. Jan. 22, 2003;19(2):185-93.

Boren T, Xiong Y, Hakam A, Wenham R, Apte S, Chan G, Kamath SG, Chen DT, Dressman H, Lancaster JM. MicroRNAs and their target messenger RNAs associated with ovarian cancer response to chemotherapy. Gynecol Oncol. May 2009;113(2):249-55.

Bou Zgheib N, Xiong Y, Marchion DC, Bicaku E, Chon HS, Stickles XB, Sawah EA, Judson PL, Hakam A, Gonzalez-Bosquet J, Wenham RM, Apte SM, Cubitt CL, Chen DT, Lancaster JM. The O-glycan pathway is associated with in vitro sensitivity to gemcitabine and overall survival from ovarian cancer. Int J Oncol. Jul. 2012;41(1):179-88.

Braakhuis BJ, Ruiz van Haperen VW, Boven E, Veerman G, Peters GJ. Schedule-dependent antitumor effect of gemcitabine in in vivo model system. Semin Oncol. Aug. 1995;22(4 Suppl 11):42-6.

Chen DT, Nasir A, Culhane A, Venkataramu C, Fulp W, Rubio R, Wang T, Agrawal D, McCarthy SM, Gruidl M, Bloom G, Anderson T, White J, Quackenbush J, Yeatman T. Proliferative genes dominate malignancy-risk gene signature in histologically-normal breast tissue. Breast Cancer Res Treat. Jan. 2010;119(2):335-46.

Chen OT, Nasir A, Cuthane A, et al: Proliferative genes dominate malignancy-risk gene signature in histologically-normal breast tissue. Breast Cancer Res Treat 119: 335-346, 2010.

Chon HS, Marchion DC, Xiong Y, Chen N, Bicaku E, Stickles XB, Bou Zgheib N, Judson PL, Hakam A, Gonzalez-Bosquet J, Wenham RM, Apte SM, Lancaster JM. The BCL2 antagonist of cell death pathway influences endometrial cancer cell sensitivity to cisplatin. Gynecol Oncol. Jan. 2012;124(1):119-24.

Cory JG, Sato A. Regulation of ribonucleotide reductase activity in mammalian cells. Mol Cell Biochem. 1983;53-54(1-2):257-66.

Davidson JD, Ma L, Flagella M, Geeganage S, Gelbert LM, Slapak CA. An increase in the expression of ribonucleotide reductase large subunit 1 is associated with gemcitabine resistance in non-small cell lung cancer cell lines. Cancer Res. Jun. 1, 2004;64(11):3761-6.

Distefano M, Ferlini C, De Vincenzo R, Gaggini C, Mancuso S, Scambia G. Antagonistic effect of the combination gemcitabine/topotecan in ovarian cancer cells. Oncol Res. 2000;12(9-10):355-9.

Dressman HK, Berchuck A, Chan G, Zhai J, Bild A, Sayer R, Cragun J, Clarke J, Whitaker RS, Li L, Gray J, Marks J, Ginsburg GS, Potti A, West M, Nevins JR, Lancaster JM. An integrated genomic-based approach to individualized treatment of patients with advanced-stage ovarian cancer. J Clin Oncol. Feb. 10, 2007;25(5):517-25.

Friedlander M, Millward MJ, Bell D, Bugat R, Harnett P, Moreno JA, Campbell L, Varette C, Ripoche V, Kayitalire L. A phase II study of gemcitabine in platinum pre-treated patients with advanced epithelial ovarian cancer. Ann Oncol. Dec. 1998;9(12):1343-5.

Fuster MM, Brown JR, Wang L, Esko JD. A disaccharide precursor of sialyl Lewis X inhibits metastatic potential of tumor cells. Cancer Res. Jun. 1, 2003;63(11):2775-81.

Gabius HJ. Cell surface glycans: the why and how of their functionality as biochemical signals in lectin-mediated information transfer. Crit Rev Immunol. 2006;26(1):43-79.

Gadducci A, Sartori E, Maggino T, Zola P, Landoni F, Fanucchi A, Palai N, Alessi C, Ferrero AM, Cosio S, Cristofani R. Analysis of failures after negative second-look in patients with advanced ovarian cancer: an Italian multicenter study. Gynecol Oncol. Feb. 1998;68(2):150-5.

Galmarini CM, Mackey JR, Dumontet C. Nucleoside analogues: mechanisms of drug resistance and reversal strategies. Leukemia. Jun. 2001;15(6):875-90.

García-Manteiga J, Molina-Arcas M, Casado FJ, Mazo A, Pastor-Anglada M. Nucleoside transporter profiles in human pancreatic cancer cells: role of hCNT1 in 2',2'-difluorodeoxycytidine-induced cytotoxicity. Clin Cancer Res. Oct. 15, 2003;9(13):5000-8.

Hofsteenge J, Müller DR, de Beer T, Löffler A, Richter WJ, Vliegenthart JF. New type of linkage between a carbohydrate and a protein: C-glycosylation of a specific tryptophan residue in human RNase Us. Biochemistry. Nov. 22, 1994;33(46):13524-30.

Huet G, Gouyer V, Delacour D, Richet C, Zanetta JP, Delannoy P, Degand P. Involvement of glycosylation in the intracellular trafficking of glycoproteins in polarized epithelial cells. Biochimie. Mar.-Apr. 2003;85(3-4):323-30.

Irizarry RA, Hobbs B, Collin F, Beazer-Barclay YD, Antonellis KJ, Scherf U, Speed TP. Exploration, normalization, and summaries of high density oligonucleotide array probe level data. Biostatistics. Apr. 2003;4(2):249-64.

Jordheim L, Galmarini CM, Dumontet C. Drug resistance to cytotoxic nucleoside analogues. Curr Drug Targets. Aug. 2003;4(6):443-60.

Jung CP, Motwani MV, Schwartz GK. Flavopiridol increases sensitization to gemcitabine in human gastrointestinal cancer cell lines and correlates with down-regulation of ribonucleotide reductase M2 subunit. Clin Cancer Res. Aug. 2001;7(8):2527-36.

Lund B, Hansen OP, Theilade K, Hansen M, Neijt JP. Phase II study of gemcitabine (2',2'difluorodeoxycytidine) in previously treated ovarian cancer patients. J Natl Cancer Inst. Oct. 19, 1994;86(20):1530-3.

Mackey JR, Mani RS, Selner M, Mowles D, Young JD, Belt JA, Crawford CR, Cass CE. Functional nucleoside transporters are required for gemcitabine influx and manifestation of toxicity in cancer cell lines. Cancer Res. Oct. 1, 1998;58(19):4349-57.

Mackey JR, Yao SY, Smith KM, Karpinski E, Baldwin SA, Cass CE, Young JD. Gemcitabine transport in xenopus oocytes expressing recombinant plasma membrane mammalian nucleoside transporters. J Natl Cancer Inst. Nov. 3, 1999;91(21):1876-81.

Marchion DC1, Cottrill HM, Xiong Y, Chen N, Bicaku E, Fulp WJ, Bansal N, Chon HS, Stickles XB, Kamath SG, Hakam A, Li L, Su D, Moreno C, Judson PL, Berchuck A, Wenham RM, Apte SM, Gonzalez-Bosquet J, Bloom GC, Eschrich SA, Sebti S, Chen DT, Lancaster JM. BAD phosphorylation determines ovarian cancer chemosensitivity and patient survival. Clin Cancer Res. Oct. 1, 2011;17(19):6356-66.

Markman M, Webster K, Zanotti K, Kulp B, Peterson G, Belinson J. Phase 2 trial of single-agent gemcitabine in platinum-paclitaxel refractory ovarian cancer. Gynecol Oncol. Sep. 2003;90(3):593-6.

McGuire WP, Hoskins WJ, Brady MF, Kucera PR, Partridge EE, Look KY, Clarke-Pearson DL, Davidson M. Cyclophosphamide and cisplatin versus paclitaxel and cisplatin: a phase III randomized trial in patients with suboptimal stage III/IV ovarian cancer (from the Gynecologic Oncology Group). Semin Oncol. Oct. 1996;23(5 Suppl 12):40-7.

Miller AB, Hoogstraten B, Staquet M, Winkler A. Reporting results of cancer treatment. Cancer. Jan. 1, 1981;47(1):207-14.

Ozols RF. The current role of gemcitabine in ovarian cancer. Semin Oncol. Apr. 2001;28(2 Suppl 7):18-24.

Patsos G, Hebbe-Viton V, Robbe-Masselot C, Masselot D, San Martin R, Greenwood R, Paraskeva C, Klein A, Graessmann M, Michalski JC, Gallagher T, Corfield A. O-glycan inhibitors generate aryl-glycans, induce apoptosis and lead to growth inhibition in colorectal cancer cell lines. Glycobiology. Apr. 2009;19(4):382-98.

Peters GJ, Bergman AM, Ruiz van Haperen VW, Veerman G, Kuiper CM, Braakhuis BJ. Interaction between cisplatin and gemcitabine in vitro and in vivo. Semin Oncol. Aug. 1995;22(4 Suppl 11):72-9.

Phelan CM1, Tsai YY, Goode EL, Vierkant RA, Fridley BL, Beesley J, Chen XQ, Webb PM, Chanock S, Cramer DW, Moysich K, Edwards RP, Chang-Claude J, Garcia-Closas M, Yang H, Wang-Gohrke S, Hein R, Green AC, Lissowska J, Carney ME, Lurie G, Wilkens LR, Ness RB, Pearce CL, Wu AH, Van Den Berg DJ, Stram DO, Terry KL, Whiteman DC, Whittemore AS, DiCioccio RA, McGuire V, Doherty JA, Rossing MA, Anton-Culver H, Ziogas A, Hogdall C, Hogdall E, Krüger Kjaer S, Blaakaer J, Quaye L, Ramus SJ, Jacobs I, Song H, Pharoah PD, Iversen ES, Marks JR, Pike MC, Gayther SA, Cunningham JM, Goodman MT, Schildkraut JM, Chenevix-Trench G, Berchuck A, Sellers TA; Ovarian Cancer Association Consortium, Australian Cancer Study (Ovarian Cancer); Australian Ovarian Cancer Study Group. Polymorphism in the

(56) References Cited

OTHER PUBLICATIONS

GALNT1 gene and epithelial ovarian cancer in non-Hispanic white women: the Ovarian Cancer Association Consortium. Cancer Epidemiol Biomarkers Prev. Feb. 2010;19(2):600-4.

Rauchwerger DR, Firby PS, Hedley DW, Moore MJ. Equilibrative-sensitive nucleoside transporter and its role in gemcitabine sensitivity. Cancer Res. Nov. 1, 2000;60(21):6075-9.

Ritzel MW, Ng AM, Yao SY, Graham K, Loewen SK, Smith KM, Hyde RJ, Karpinski E, Cass CE, Baldwin SA, Young JD. Recent molecular advances in studies of the concentrative Na+-dependent nucleoside transporter (CNT) family: identification and characterization of novel human and mouse proteins (hCNT3 and mCNT3) broadly selective for purine and pyrimidine nucleosides (system cib). Mol Membr Biol. Jan.-Mar. 2001;18(1):65-72.

Ruiz van Haperen VW, Veerman G, Boven E, Noordhuis P, Vermorken JB, Peters GJ. Schedule dependence of sensitivity to 2',2'-difluorodeoxycytidine (Gemcitabine) in relation to accumulation and retention of its triphosphate in solid tumour cell lines and solid tumours. Biochem Pharmacol. Oct. 7, 1994;48(7):1327-39.

Ruiz van Haperen VW, Veerman G, Eriksson S, Boven E, Stegmann AP, Hermsen M, Vermorken JB, Pinedo HM, Peters GJ. Development and molecular characterization of a 2',2'-difluorodeoxycytidine-resistant variant of the human ovarian carcinoma cell line A2780. Cancer Res. Aug. 1, 1994;54(15):4138-43.

Ruiz van Haperen VW, Veerman G, Eriksson S, Stegmann AP, Peters GJ. Induction of resistance to 2',2'-difluorodeoxycytidine in the human ovarian cancer cell line A2780. Semin Oncol. Aug. 1995;22(4 Suppl 11):35-41.

Rustin GJ, Nelstrop AE, Bentzen SM, Piccart MJ, Bertelsen K. Use of tumour markers in monitoring the course of ovarian cancer. Ann Oncol. 1999;10 Suppl 1:21-7.

Rustin GJ, Nelstrop AE, McClean P, Brady MF, McGuire WP, Hoskins WJ, Mitchell H, Lambert HE. Defining response of ovarian carcinoma to initial chemotherapy according to serum CA 125. J Clin Oncol. May 1996;14(5):1 545-51.

Sato J, Kimura T, Saito T, Anazawa T, Kenjo A, Sato Y, Tsuchiya T, Gotoh M. Gene expression analysis for predicting gemcitabine resistance in human cholangiocarcinoma. J Hepatobiliary Pancreat Sci. Sep. 2011;18(5):700-11.

Thelander L, Berg P. Isolation and characterization of expressible cDNA clones encoding the M1 and M2 subunits of mouse ribonucleotide reductase. Mol Cell Biol. Oct. 1986;6(10):3433-42.

Ulloa F, Real FX. Benzyl-N-acetyl-alpha-D-galactosaminide induces a storage disease-like phenotype by perturbing the endocytic pathway. J Biol Chem. Apr. 4, 2003;278(14):12374-83.

van der Wilt CL1, Kroep JR, Bergman AM, Loves WJ, Alvarez E, Talianidis I, Eriksson S, van Groeningen CJ, Pinedo HM, Peters GJ. The role of deoxycytidine kinase in gemcitabine cytotoxicity. Adv Exp Med Biol. 2000;486:287-90.

van Moorsel CJ, Veerman G, Bergman AM, Guechev A, Vermorken JB, Postmus PE, Peters GJ. Combination chemotherapy studies with gemcitabine. Semin Oncol. Apr. 1997;24(2 Suppl 7):57-17-57-23.

Varki A. Biological roles of oligosaccharides: all of the theories are correct. Glycobiology. Apr. 1993;3(2):97-130.

Wells L, Hart GW. O-GlcNAc turns twenty: functional implications for post-translational modification of nuclear and cytosolic proteins with a sugar. FEBS Lett. Jul. 3, 2003;546(1):154-8.

Zhou BS, Tsai P, Ker R, Tsai J, Ho R, Yu J, Shih J, Yen Y. Overexpression of transfected human ribonucleotide reductase M2 subunit in human cancer cells enhances their invasive potential. Clin Exp Metastasis. Jan. 1998;16(1):43-9.

International Search Report and Written Opinion of the International Searching Authority from related application No. PCT/US2013/035470, dated Jun. 28, 2013.

Wang PH, Lee WL, Juang CM, Yang YH, Lo WH, Lai CR, Hsieh SL, Yuan CC. Altered mRNA expressions of sialyltransferases in ovarian cancers. Gynecol Oncol. Dec. 2005;99(3):631-9.

* cited by examiner

O-GLYCAN PATHWAY OVARIAN CANCER SIGNATURE

CROSS-REFERENCE TO RELATED APPLICATIONS

This application claims benefit of U.S. Provisional Application No. 61/620,757, filed Apr. 5, 2012, which is hereby incorporated herein by reference in its entirety.

STATEMENT REGARDING FEDERALLY SPONSORED RESEARCH OR DEVELOPMENT

This invention was made with Government Support under Agreement CA110499 awarded by the National Institutes of Health, and under Agreement DAMD17-02-2-0051 awarded by the US Army Medical Research and Materiel Command. The Government has certain rights in the invention.

BACKGROUND

Ovarian cancer (OVCA) is the leading cause of gynecologic cancer mortality and the sixth most common cancer diagnosed in women in the United States. Advanced-stage epithelial OVCA is highly heterogeneous at a clinical, biologic, and genetic level, but patients are currently treated in a uniform fashion with cytoreductive surgery and platinum/taxane-based combination chemotherapy. Unfortunately, most patients ultimately succumb to persistent or recurrent platinum-resistant disease (Gadducci A, et al. Gynecol Oncol 68: 150-5, 1998; McGuire W P, et al. N Engl J Med 334: 1-6, 1996). Currently, efforts to develop therapeutic agents with greater efficacy against platinum-resistant disease are limited because of incomplete understanding of the molecular determinants of OVCA drug response.

Gemcitabine (2',2'-difluorodeoxycytidine), a synthetic nucleoside analog of cytidine, is frequently used as a second-line therapy for patients with relapsed OVCA (Ozols R F. Semin Oncol 28: 18-24, 2001). As a pyrimidine analogue, gemcitabine replaces the nucleic acid cytidine during DNA replication, blocking processing and chain elongation by the DNA polymerase complex, resulting in G1 arrest and a subsequent cytostatic effect. Additionally, the gemcitabine triphosphate metabolite is incorporated into RNA, thus inhibiting RNA synthesis (Mackey J R, et al. Cancer Res 58: 4349-57, 1998). Gemcitabine efficacy has been evaluated extensively both in vitro and in vivo against OVCA (Distefano M, et al. Oncol Res 12: 355-9, 2000; Peters G J, et al. Semin Oncol 22: 72-9, 1995; Ruiz van Haperen V W, et al. Biochem Pharmacol 48: 1327-39, 1994; Ruiz van Haperen V W, et al. Cancer Res 54: 4138-43, 1994). Gemcitabine has demonstrated single-agent activity against OVCA cell lines (Ruiz van Haperen V W, et al. Semin Oncol 22: 35-41, 1995) and synergistic activity with several other antineoplastic agents, including platinum compounds, topotecan, and etoposide (van Moorsel C J, et al. Semin Oncol 24: S7-17-S7-23, 1997). In animal tumor models, the gemcitabine effect has been shown to be schedule-dependent, and continuous infusions over 24 hours appear to enhance gemcitabine cytotoxicity (Braakhuis B J, et al. Semin Oncol 22: 42-6, 1995). Phase II and III studies of gemcitabine (800-1250 mg/m$^2$/week) in patients with recurrent OVCA have demonstrated response rates up to 19% (Friedlander M, et al. Ann Oncol 9: 1343-5, 1998; Lund B, et al. J Natl Cancer Inst 86: 1530-3, 1994; Markman M, et al. Gynecol Oncol 90: 593-6, 2003). Despite such data, the molecular determinants of gemcitabine activity remain to be fully elucidated.

Tailored strategies are needed that stratify patients based on their molecular fingerprints, e.g., those with the "highest risk" disease, those who may benefit from additional pathway-targeted therapy added to standard of care cytotoxic regimens, and those who may (or may not) benefit from aggressive surgical interventions.

SUMMARY

Biomarkers, methods, assays, and kits are provided for determining the prognosis of a patient with ovarian cancer and treating the ovarian cancer. The assays and kits can contain primers, probes, or binding agents for detecting expression of genes listed in Table 2.

In particular, the disclosed method can involve assaying a biological sample from the subject for the expression level of O-glycan biosynthesis pathway (OGBP) genes, such as those selected from the group consisting of B3GALT1, B3GALT2, B3GALT4, B3GALT5, B3GNT6, B4GALT1, B4GALT2, B4GALT3, C1GALT1, GALNT1, GALNT10, GALNT11, GALNT12, GALNT13, GALNT14, GALNT2, GALNT3, GALNT4, GALNT5, GALNT6, GALNT7, GALNT8, GALNT9, GALNTL1, GALNTL2, GALNTL4, GALNTL5, GCNT1, GCNT2, GCNT3, ST3GAL1, ST3GAL2, ST6GALN, and WBSCR17. The expression levels of these genes can be compared to control values to produce a gene profile, which can be analyzed to calculate an OGBP score.

In some embodiments of this method, a high OGBP score can be an indication of a favorable prognosis for the patient. For example, a favorable prognosis can involve an increased likelihood of survival after treatment with surgery and/or chemotherapy.

In some embodiments, the method involves optimally debulking the ovarian cancer only if the patient has a high OGBP score. In cases where the patient has a low OGBP score, the method can comprise either not debulking or only suboptimally debulking the ovarian cancer if the patient has a low OGBP score. Suboptimal debulking has been shown to provide equivalent prognosis to chemotherapy. Therefore, in some cases, the patient may be treated with chemotherapy instead of debulking if the patient has a low OGBP score since they are not likely to benefit from either optimal debulking or the combination of debulking and chemotherapy. Patients with a high OGBP score may be debulked (optimally or suboptimally) and treated with chemotherapy since they are more likely to benefit from the aggressive treatment strategy.

Biomarkers, methods, assays, and kits are also provided for predicting the sensitivity of ovarian cancer cells to chemotherapy. In particular, the method can involve assaying the ovarian cancer cells for the expression level of the genes listed in Table 3. The expression levels of these genes can be compared to control values to produce a gene profile, which can be analyzed to calculate a sensitivity score. In some embodiments, a high sensitivity score is an indication that the ovarian cancer cells are sensitive to the chemotherapy and a low sensitivity score is an indication that the ovarian cancer cells are chemoresistant to the chemotherapy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
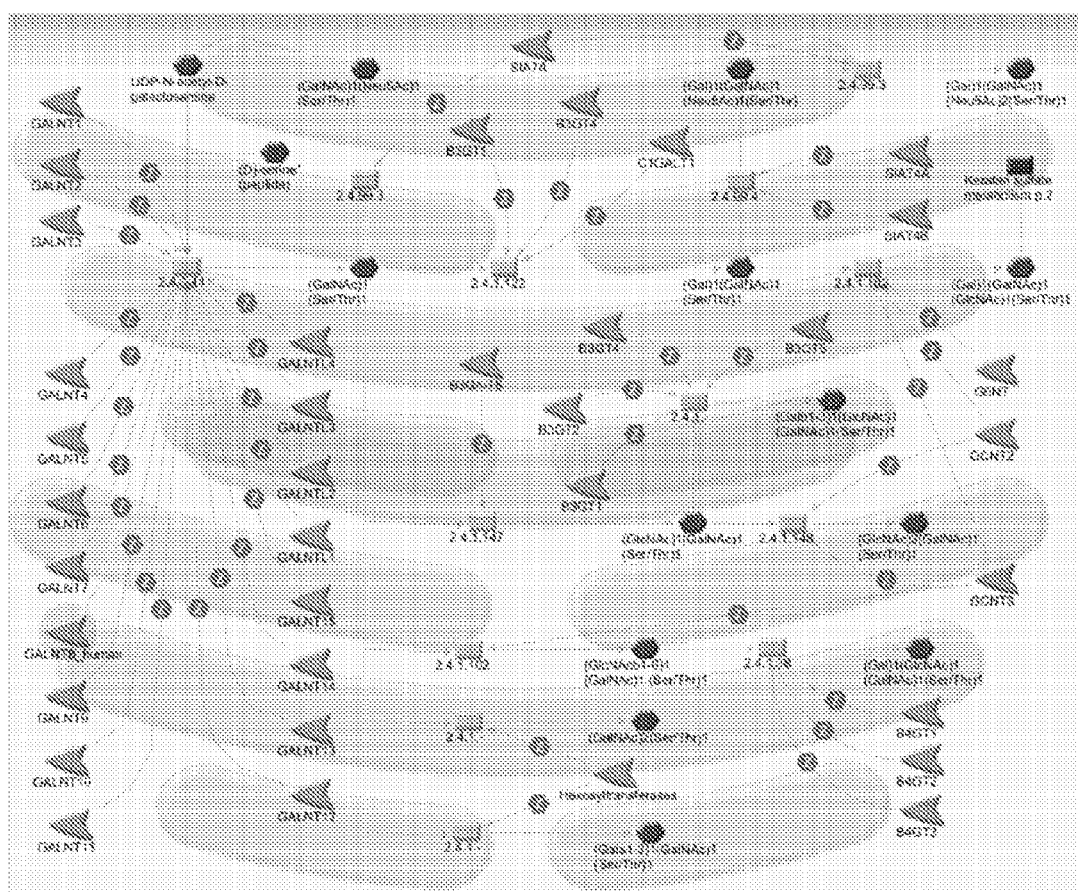
FIG. 1 is a schematic depicting the O-glycan biosynthesis/human version pathway.

Biomarkers, methods, assays, and kits are provided for determining the prognosis of, and treating a patient with, ovarian cancer. In some embodiments, the disclosed methods relate to any primary cancer in the ovary. The ovarian cancer can also be a secondary cancer, i.e., cancer cells that metastasized from the ovary to other tissue, or cancer cells metastasized from other tissue into the ovary.

The term "subject" refers to any individual who is the target of administadministration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The majority of ovarian cancers are surface epithelial-stromal tumors (ovarian adenocarcinoma). For example, the ovarian cancer can be a cystadenocarcinoma (most common), "borderline" adenocarcinoma, endometrioid tumor, papilloma, clear-cell ovarian tumor, and mucinous adenocarcinoma. In other embodiments, the ovarian cancer may be a carcinoma, mullerian tumor, germ cell tumor (e.g., teratoma or dysgerminoma), squamous cell carcinoma, or Brenner tumor.

The ovarian cancer can be a Stage I (T1a, T1b, T1c), Stage II (T2a, T2b, T2c), Stage III (T3a, T3b, T3c), or Stage IV ovarian cancer (as determined by the FIGO or AJCC staging system). In some embodiments, the methods are particularly useful in patients with advanced-stage (Stage III or IV) ovarian cancer as demonstrated in the Examples below.

The disclosed method can involve assaying a biological sample from the patient for the expression level of O-glycan biosynthesis pathway (OGBP) genes, such as those selected from the group consisting of B3GALT1, B3GALT2, B3GALT4, B3GALT5, B3GNT6, B4GALT1, B4GALT2, B4GALT3, C1GALT1, GALNT1, GALNT10, GALNT11, GALNT12, GALNT13, GALNT14, GALNT2, GALNT3, GALNT4, GALNT5, GALNT6, GALNT7, GALNT8, GALNT9, GALNTL1, GALNTL2, GALNTL4, GALNTL5, GCNT1, GCNT2, GCNT3, ST3GAL1, ST3GAL2, ST6GALN, and WBSCR17. The method can involve assaying a sufficient number of the OGBP genes to provide a statistically significant OGBP score, as described below. For example, the method can involve assaying the biological sample from the patient for the expression level of at least 2, 10, 20, 30, 31, 32, 33, or 34 OGBP genes, including 2, 10, 20, 30, 31, 32, 33, 34, or more of OGBP genes.

The term "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. In preferred embodiments, the biological sample is a tumor biopsy.

Methods of determining gene expression levels include methods that quantify mRNA, either directly by detecting RNA, or indirectly by detecting cDNA reverse transcripts. A measured expression level may be expressed as any qualitative or quantitative value, for example, a fold-change in expression, up or down, relative to a threshold value, or a log ratio of expression, or any visual representation thereof, such as, for example, a "heatmap" where a color intensity is representative of the amount of gene expression detected. Exemplary methods for detecting the level of expression of a gene include, but are not limited to, Northern blotting, dot or slot blots, reporter gene matrix, nuclease protection, microarray profiling, differential display, and MNAzyme-based detection methods. Optionally a gene whose level of expression is to be detected may be amplified, for example by methods that may include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

The data may be obtained via any technique that results in an individual receiving data associated with a sample. For example, an individual may obtain the dataset by generating the dataset himself by methods known to those in the art. Alternatively, the dataset may be obtained by receiving a dataset or one or more data values from another individual or entity. For example, a laboratory professional may generate certain data values while another individual, such as a medical professional, may input all or part of the dataset into an analytic process to generate the result.

A number of suitable high throughput formats exist for evaluating gene expression. Generally, such methods involve a logical or physical array of oligonucleotides (e.g., primers or probes), the subject samples, or both. Common array formats include both liquid and solid phase arrays. For example, assays employing liquid phase arrays, e.g., for hybridization of nucleic acids, can be performed in multi-well or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., xMAP® technology from Luminex (Austin, Tex.), the SECTOR® Imager with MULTI-ARRAY® and MULTI-SPOT® technologies from Meso Scale Discovery (Gaithersburg, Md.), the ORCA™ system from Beckman-Coulter, Inc. (Fullerton, Calif.) and the ZYMATE™ systems from Zymark Corporation (Hopkinton, Mass.), miRCURY LNA™ microRNA Arrays (Exiqon, Woburn, Mass.).

A variety of solid phase arrays can favorably be employed to determine expression patterns in the context of the disclosed methods, assays and kits. Exemplary formats include membrane or filter arrays (e.g., nitrocellulose, nylon), pin arrays, and bead arrays (e.g., in a liquid "slurry"). Typically, oligonucleotide probes corresponding to gene product are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In some embodiments, the array is a "chip" composed, e.g., of one of the above-specified materials. Polynucleotide probes, e.g., RNA, cDNA, or oligonucleotides that specifically interact with expression products may be affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Microarray expression may be detected by scanning the microarray with a variety of laser or CCD-based scanners, and extracting features with numerous software packages, for example, IMAGENE™ (Biodiscovery), Feature Extraction Software (Agilent), SCANLYZE™ (Stanford Univ., Stanford, Calif.), GENEPIX™ (Axon Instruments).

From these gene expression values, a dataset can be generated and inputted into an analytical classification process that uses the data to classify the biological sample with a risk score (e.g., OGBP score or sensitivity score).

A risk score can be determined using standard statistical methods, such as multivariate analysis. In some embodiments, the risk score is a regression value, where a regression value of about 1 (e.g., at least 0.7, 0.8, 0.9, or 1) is a "high" risk score (e.g., high OGBP score) and a regression value of about 0 (e.g., less than 0, 0.1, 0.2, or 0.3) is a "low" risk score (e.g., low OGBP score).

The gene profile may also be analyzed by principal component analysis to derive a risk score. Principal component analysis (PCA) is a mathematical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it be orthogonal to (i.e., uncorrelated with) the preceding components. When used in the disclosed methods, a PCA score can be a numeric value that summarizes the gene expression of the entire panel (e.g., OGBP, Table 2) for that patient's biological sample. Therefore, in these embodiments, a "high" risk score (e.g., high OGBP score) may be a PCA score above the median value, and a "low" risk score (e.g., low OGBP score) may be a PCA score below the median value.

For example, PCA can be used to reduce gene expression values into a small set of uncorrelated principal components based on their ability to account for variation. The first principal component (1st PCA), as it accounts for the largest variability in the data, can be to represent the overall expression level for the set of genes. For example, OGBP score can be $\Sigma w_i x_i$, a weighted average expression among the OGBP genes, where $x_i$ represents gene i expression level, $w_i$ is the corresponding weight (loading coefficient) with $\Sigma w^2_i = 1$, and the $w_i$ values maximize the variance of $\Sigma w_i x_i$.

In some embodiments, the gene expression values involve numerous data points that are best managed and stored in a computer readable form. Therefore, in preferred embodiments, the risk score is a regression value derived from the gene expression values as a weighted function of the quantified expression values. The weighted function can be derived from linear regression analysis of experimental results comparing gene expression of patients with a good prognosis versus those with poor prognosis. Each gene expression value species can be multiplied by a weighting constant and summed.

Prior to analysis, the data in each dataset can be collected by measuring the values for each gene, usually in duplicate or triplicate or in multiple replicates. The data may be manipulated, for example raw data may be transformed using standard curves, and the average of replicate measurements used to calculate the average and standard deviation for each patient. These values may be transformed before being used in the models, e.g. log-transformed, Box-Cox transformed, etc. This data can then be input into an analytical process with defined parameter.

The analytic classification process may be any type of learning algorithm with defined parameters, or in other words, a predictive model. In general, the analytical process will be in the form of a model generated by a statistical analytical method such as those described below. Examples of such analytical processes may include a linear algorithm, a quadratic algorithm, a polynomial algorithm, a decision tree algorithm, or a voting algorithm.

Using any suitable learning algorithm, an appropriate reference or training dataset can be used to determine the parameters of the analytical process to be used for classification, i.e., develop a predictive model. The reference or training dataset to be used will depend on the desired classification to be determined. The dataset may include data from two, three, four or more classes.

The number of features that may be used by an analytical process to classify a test subject with adequate certainty is 2 or more. In some embodiments, it is 3 or more, 4 or more, 10 or more, or between 10 and 200. Depending on the degree of certainty sought, however, the number of features used in an analytical process can be more or less, but in all cases is at least 2. In one embodiment, the number of features that may be used by an analytical process to classify a test subject is optimized to allow a classification of a test subject with high certainty.

Suitable data analysis algorithms are known in the art. In one embodiment, a data analysis algorithm of the disclosure comprises Classification and Regression Tree (CART), Multiple Additive Regression Tree (MART), Prediction Analysis for Microarrays (PAM), or Random Forest analysis. In other embodiments, a data analysis algorithm of the disclosure comprises ANOVA and nonparametric equivalents, linear discriminant analysis, logistic regression analysis, nearest neighbor classifier analysis, neural networks, principal component analysis, hierarchical cluster analysis, quadratic discriminant analysis, regression classifiers and support vector machines.

As will be appreciated by those of skill in the art, a number of quantitative criteria can be used to communicate the performance of the comparisons made between a gene profile and control values. These include area under the curve (AUC), hazard ratio (HR), relative risk (RR), reclassification, positive predictive value (PPV), negative predictive value (NPV), accuracy, sensitivity and specificity, Net reclassification Index, Clinical Net reclassification Index. In addition, other constructs such a receiver operator curves (ROC) can be used to evaluate analytical process performance.

Ovarian cancer usually has a relatively poor prognosis. It is disproportionately deadly because it lacks any clear early detection or screening test, meaning that most cases are not diagnosed until they have reached advanced stages. More than 60% of women presenting with this cancer have stage III or stage IV cancer, when it has already spread beyond the ovaries. Ovarian cancers shed cells into the naturally occurring fluid within the abdominal cavity. These cells can then implant on other abdominal (peritoneal) structures, included the uterus, urinary bladder, bowel and the lining of the bowel wall omentum forming new tumor growths before cancer is even suspected.

The five-year survival rate for all stages of ovarian cancer is 47%. In some embodiments of the disclosed method, a high OGBP score can be an indication of a favorable prognosis for the patient. A favorable prognosis can involve an increased likelihood of survival after treatment with chemotherapy. For example, a favorable prognosis can be a greater than 47%, 48%, 49%, 50%, 60%, 70%, 80%, or 90% chance of survival for at least five years.

Debulking (a.k.a. cytoreduction or cytoreductive surgery) is a surgical procedure to treat ovarian cancer that usually involves removing not only the ovaries but also the uterus, cervix, fallopian tubes, and as much visible disease as possible. In advanced malignancy, where complete resection is not feasible, as much tumor as possible is removed. However, the goal is to leave no tumor nodule behind that measures more than one centimeter. When less than 1 cm in diameter of tumor is left behind, this is referred to as optimal, aggressive, or ultraradical debulking. When greater than 1 cm in diameter of tumor is left behind, this is referred to as suboptimal debulking.

Optimal debulking is not always feasible due to the location and risk of complications. The ability to predict whether optimal debulking will make a significant difference in prognosis can therefore be useful to assist the physician in making the determination whether to settle for suboptimal debulking. In some embodiments, the method involves optimally debulking the ovarian cancer only if the patient has a high OGBP score. In cases where the patient has a low OGBP score, the method can comprise either not debulking or only suboptimally debulking the ovarian cancer if the patient has a low OGBP score. Suboptimal debulking has been shown to provide equivalent prognosis to chemotherapy. Therefore, in some cases, the patient may be treated with chemotherapy instead of debulking if the patient has a low OGBP score. Patients with a high OGBP score may be debulked (optimal or suboptimal) and treated with chemotherapy.

The term "chemotherapy" refers to a cytotoxic antineoplastic drug that may be give for curative or palliative treatment of cancer. The term includes adjuvant and neoadjuvant agents that are given in combination with surgery and/or radiotherapy. In particular embodiments, the chemotherapy is effective against ovarian cancer. In some cases, the chemotherapy is a combination of a platinum-based drug, such as carboplatin or cisplatin, with a taxane, such as paclitaxel or docetaxel, or a nucleoside analog, such as gemcitabine. Therefore, in some embodiments, the chemotherapy contains gemcitabine, including a combination of gemcitabine and cisplatin. Other drugs that may be used as chemotherapeutics for treatment of ovarian cancer include albumin bound paclitaxel (nab-paclitaxel), altretamine, capecitabine, cyclophosphamide, etoposide, ifosfamide, irinotecan, liposomal doxorubicin, melphalan, pemetrexed, topotecan, and vinorelbine.

Biomarkers, methods, assays, and kits are also provided for predicting the sensitivity of ovarian cancer cells to chemotherapy. In particular, the method can involve assaying the ovarian cancer cells for the expression level of the genes listed in Table 3. The expression levels of these genes can be compared to control values to produce a gene profile, which can be analyzed to calculate a sensitivity score. In some embodiments, a high sensitivity score is an indication that the ovarian cancer cells are sensitive to the chemotherapy and a low sensitivity score is an indication that the ovarian cancer cells are chemoresistant to the chemotherapy. As above, the method can involve assaying a sufficient number of the genes to provide a statistically significant sensitivity score, as described below. For example, the method can involve assaying the biological sample from the patient for the expression level of at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 121, 122, 123, 124, 125, 126, 127, 128, 129, 130, or 131 of the genes listed in Table 3.

A high OGBP score is also shown herein to be associated with resistance to chemotherapy, such as gemcitabine. Therefore, in some embodiments, the method involves treating the patient with chemotherapy only if the patient has a low OGBP score, a high sensitivity score, or a combination thereof.

A number of embodiments of the invention have been described. Nevertheless, it will be understood that various modifications may be made without departing from the spirit and scope of the invention. Accordingly, other embodiments are within the scope of the following claims.

EXAMPLES

Example 1

In this study, the goal was to determine the molecular underpinnings of OVCA response to gemcitabine at a genome-wide level. The genes and molecular signaling pathways associated with the response of OVCA cells was investigated in vitro to gemcitabine and a study was conducted to determine how these pathways influence in vivo clinical outcomes for patients with this disease.

Materials and Methods

Overview.

Forty one (41) OVCA cell lines were subjected to gene expression analysis and, in parallel, gemcitabine sensitivity ($IC_{50}$) was measured. Genes associated with baseline gemcitabine sensitivity, identified by Pearson's correlation analysis, were subjected to molecular pathway analysis. Expression of identified pathways were evaluated using a series of clinico-genomic datasets from 142 patients with stage III/IV serous OVCA. All 142 patients had signed the IRB-approved, written informed consent forms.

Primary OVCA Patient Samples.

Genome-wide expression data was evaluated from 142 patients treated at Duke and Moffitt Cancer Centers (including 114, previously reported, Dressman et al. 2007 (Dressman H K, et al. J Clin Oncol 25: 517-525, 2007), and 28 new samples) (Chon H S, et al. Gynecol Oncol 124: 119-124, 2011). Patients treated at Duke and Moffitt Cancer Centers for whom genomic data were analyzed in the current study had a mean age of 56 years and included 101 patients who demonstrated a CR to primary therapy and 41 who demonstrated an IR. Cytoreductive surgery was optimal for 73 patients and suboptimal for 68. The number of patients with grade 1 disease was 6, grade 2 was 61, grade 3 was 73, with grade unknown for two patients. Race data for this group included: Caucasian, 117; African-American, 18; Asian, 4; Hispanic, 1; and unknown, 2. Inclusion criteria for all 142 patients (including those treated at Moffitt, Duke) included: a pathologically confirmed diagnosis of serous epithelial ovarian cancer, age >18 years, surgically confirmed advanced stage (III/IV) disease, primary surgical cytoreductive surgery prior to chemotherapy, and primary chemotherapy with a platinum-based regimen (+/− taxane or cyclophosphamide). Exclusion criteria for all 142 patients (including those treated at Moffitt, Duke) included: non-epithelial cancer, borderline tumors, non-serous tumors, early stage (I/II) disease, absence of pathologic documentation of diagnosis, recurrent disease, receipt of neoadjuvant chemotherapy, and unknown clinical response to primary therapy.

Defining Clinical Response.

Using medical record review, overall survival was evaluated and all 289 OVCA samples were characterized as CR or incomplete responder (IR) to primary platinum-based therapy using criteria described previously (Dressman H K, et al. J Clin Oncol 25: 517-525, 2007). Clinical response to primary therapy (surgery plus platinum-based chemotherapy) was therefore established for all 289 patients using standard WHO criteria for patients with measurable disease (Miller A B, et al. Cancer 47: 207-214, 1981). CA-125 was used to classify responses only in the absence of a measurable lesion (e.g. patients subject to optimal cytoreductive surgery); CA-125 response criteria were based on established guidelines (Rustin G J, et al. Ann Oncol 10 Suppl 1: 21-27, 1999; Rustin G J, et al. J Clin Oncol 14: 1545-1551, 1996). A complete-response (CR) was defined as a complete disappearance of all measurable and assessable disease or, in the absence of measurable lesions, a normalization of the CA-125 level after adjuvant therapy. Patients were considered to have an incomplete-response (IR) if they demonstrated only a partial response, had stable disease, or demonstrated progressive disease during primary therapy. A partial response was considered a 50% or greater reduction in the product obtained from measurement of each bi-dimensional lesion for at least 4 weeks or a decrease in the CA-125 level by at least 50% for at least 4 weeks. Disease progression was defined as a 50% or greater increase in the product from any lesion documented within 8 weeks of initiation of therapy, the appearance of any new lesion within 8 weeks of initiation of therapy, or any increase in the CA-125 from baseline at initiation of therapy. Stable disease was defined as disease not meeting any of the above criteria. All tissues, acquired with Institutional Review Board approval, were processed as previously reported (Dressman H K, et al. J Clin Oncol 25: 517-525, 2007; Boren T, et al. Gynecol Oncol 113: 249-255, 2009). Microarray gene expression data (Affymetrix® HG-U133A) were analyzed for 142 patients (114 samples previously reported (Dressman H K, et al. J Clin Oncol 25: 517-525, 2007) and 28 Moffitt Cancer Center (MCC) samples; GEO accession number GSE23554).

Cell Culture.

OVCA cell lines were obtained from the American Type Culture Collection (Manassas, Va.; CAOV3, OV90, OVCAR3, SKOV3), from the European Collection of Cell Cultures (Salisbury, UK; A2780CP, A2780S), from Kyoto University (Kyoto, Japan; CHI, CHIcisR, M41, M41CSR, Tyknu, and TyknuCisR), or as kind gifts (A2008, C13, CAOV2, HeyA8, IGR-OV1, IMCC3, IMCC5, MCAS, OV2008, OVCA420, OVCA429, OVCA432, OVCA433, FUOV1, PEO1, PEO4, SK-OV-6, T8, TOV-112D, TOV-21-G, Dov13, BG1, Ovary1847, OVCAR10, OVCAR8, OVCAR5, OVCAR4, OVCAR2, SK-OV-4). Cell lines were maintained in RPMI 1640 medium (Invitrogen, Carlsbad, Calif.) supplemented with 10% fetal bovine serum (Fisher Scientific, Pittsburgh, Pa.), 1% sodium pyruvate, 1% penicillin/streptomycin (Cellgro, Manassas, Va.), and 1% non-essential amino acids (HyClone, Hudson, N.H.). Mycoplasma testing was performed every 6 months, in accordance with the manufacturer's protocol (Lonza, Rockland, Me.).

RNA Extraction and Microarray Expression Analysis.

RNA from 41 OVCA cell lines was extracted using the RNeasy™ kit following manufacturer's recommendations (Qiagen, Valencia, Calif.). Quality of the RNA was measured using an Agilent 2100 Bioanalyzer. The targets for Affymetrix® DNA microarray analysis were prepared according to the manufacturer's instructions, and targets were hybridized to customized Human Affymetrix® HuRSTA gene chips (HuRSTA-2a520709), which include 60,607 probe sets and representation of 19,308 genes (Gene Expression Omnibus accession number GSE34615).

CellTiter-Blue Cell Viability Assays.

Drug activity was evaluated using a high-throughput CellTiter-Blue® cell viability assay. Cells ($2.5 \times 10^3$ per well) were plated in 384-well plates using complete media with 10% fetal bovine serum and allowed to adhere overnight. After cell adherence, increasing concentrations of gemcitabine were added to appropriate wells using an automated pipetting station. Four replicate wells were used for each drug concentration and for vehicle controls. Drug dilutions initially consisted of 1.5-fold serial dilutions from a maximum concentration of 100 μM. The cells were incubated with the drug for 72 hours, and 5 μA of CellTiter-Blue® reagent (Promega Corp) were added to each well. Fluorescence was read at 579-nm excitation/584-nm emission using a Synergy™ 4 microplate reader (Bio-Tek Instruments, Inc., Winooski, Vt.). $IC_{50}$ values were determined using a sigmoidal equilibrium model fit (XLfit 5.2, ID Business Solutions Ltd.). The $IC_{50}$ was defined as the concentration of drug required for a 50% reduction in growth/viability.

Statistical Analysis.

Expression data from 41 OVCA cell lines were subjected to background correction and normalization using the "Robust Multichip Average" algorithm in the Affymetrix® Expression Console. Pearson's correlation test was performed on individual gene expression and $IC_{50}$ values. Probe sets with p<0.001 were considered to have significant correlations with $IC_{50}$ values and were uploaded to Meta-Core™ GeneGo for pathway analysis. Pathways with p<0.05 were considered significant, based upon the GeneGo/MetaCore™ statistical test for significance.

Development and Evaluation of Pathway Gene Signatures.

Using genomic data from the panel of 41 OVCA cells, principal component analysis was used to derive: O-glycan biosynthesis/Human version pathway gene expression signature. Principal components analysis (PCA) methodology was used to derive a pathway gene expression signature with a corresponding "pathway score" to represent an overall gene expression level for the pathway genes. The generation of the signature used data from cell lines only; no patient data were used. That is, no data from the Duke/MCC samples were used in the initial development/generation of the O-glycan biosynthesis/Human version pathway signature; the Duke/MCC ovarian data was a completely independent evaluation set. Specifically, using genomic and $IC_{50}$ data from 41 OVCA cell lines, Pearson correlation was used to identify genes associated with sensitivity ($IC_{50}$) to gemcitabine. Expression was calculated using the robust multi-array average algorithm (Irizarry R A, et al. Biostatistics 4: 249-264, 2003) implemented in Bioconductor extensions to the R-statistical programming environment as described previously (Bolstad B M, et al. Bioinformatics 19: 185-193, 2003). Probe sets with expression ranges <2-fold (maximum/minimum) and control probes (i.e., AFFX_*probe sets) were excluded from the analysis. For each cell line, Pearson correlation coefficients were calculated for expression data and drug $IC_{50}$. Genes/probe sets demonstrating expression/$IC_{50}$ correlations (|R|>0.85) were subjected to biological pathway analysis using GeneGo/MetaCore™ software, and maps/pathways were identified using the GeneGo/MetaCore™ statistical test for significance (P<0.001). In this way, O-glycan biosynthesis/Human version pathway was found to be associated (P=0.0013) with cell line drug sensitivity. To build pathway-specific PCA scores for O-glycan pathway, initially GeneGo/MetaCore™-defined objects (genes) within each of the pathways (associated with OVCA cell line $IC_{50}$) were identified. Next, for each pathway object identified in this way, all probe sets were selected and used for generation of the PCA score. For the O-glycan pathway, 64 probe sets represented 34 genes. Principal component analysis was performed using all 64 probe sets to reduce data dimension into a small set of uncorrelated principal components for both pathways. These sets of principal components were generated based on their ability to account for variation. The first principal component (1st PCA), as it accounts for the largest variability in the data, was used as a pathway score to represent the overall expression level for the pathway. That is, pathway score=$\Sigma w_i x_i$, a weighted average expression among the O-glycan biosynthesis/Human version pathway genes (independently for each pathway), where $x_i$ represents gene i expression level, $w_i$ is the corresponding weight (loading coefficient) with $\Sigma w^2_i = 1$, and the $w_i$ values maximize the variance of $\Sigma w_i x_i$. This approach has been used to derive a malignancy pathway gene signature in a breast cancer study (Chen D T, et al. Breast Cancer Res Treat 119: 335-346). The O-glycan pathway gene expression signature scores developed in OVCA cell lines were evaluated in an independent set of 142 OVCA samples from MCC and Duke University Medical Center (OVCA 142 dataset). For the clinical-genomic OVCA dataset, log-rank test with Kaplan-Meier survival curves was used to test any association between the O-glycan pathway score ("high versus "low" based upon a median value cut-off) and overall survival for patients with OVCA.

Validation of Signatures in Primary OVCA Datasets.

The pathway gene expression signature scores were evaluated in an independent publicly available clinico-genomic dataset from 142 OVCA samples (Dressman H K, et al. J Clin Oncol 25: 517-25, 2007; Marchion D C, et al. Clin Cancer Res). In brief, all 142 samples were known to have been resected from patients with advanced-stage (III/IV), serous epithelial OVCA, who underwent primary cytoreductive surgery followed by primary therapy with a platinum-based regimen (+/− taxane or cyclophosphamide). Response to this primary therapy [complete response (CR) versus incomplete response (IR)] has previously been described for these patients (Marchion D C, et al. Clin Cancer Res). In brief, patients who demonstrated a CR had no evidence of disease on physical examination, serum tumor marker monitoring, or radiographic imaging. The IR category included all other patients. Log-rank tests with Kaplan-Meier survival curves were used to test any association between the pathway scores ("high" versus "low" based on a median value cut-off) and overall survival for patients with OVCA.

Results

Forty-one OVCA cell lines were treated with increasing concentrations of gemcitabine, and the $IC_{50}$ values were determined (Table I). Pearson's correlation test using gemcitabine $IC_{50}$ and OVCA cell line gene expression data identified 131 unique genes to be associated with gemcitabine sensitivity (p<0.001; Supplementary Table). GeneGo MetaCore™ analysis identified three biological pathways that were represented within the 131 genes associated with gemcitabine sensitivity (p<0.02). These molecular signaling pathways included O-glycan biosynthesis (p=0.001), Cell cycle_Role of Nek in cell cycle regulation (p=0.005), and Immune response_Antiviral actions of Interferons (p=0.01). Statistical significance was derived from the total number of genes input into the pathway analysis software, the number of input genes present in a specific pathway, and the actual number of genes in that pathway. Thus, the p value represents the probability that mapping a set of genes to a particular pathway occurs by chance. The O-glycan pathway demonstrated the highest level of statistical significance in its association with sensitivity to gemcitabine (p=0.001) (FIG. 1).

Expression of the O-Glycan Pathway is Associated with OVCA Clinical Outcome.

Figure 2A:
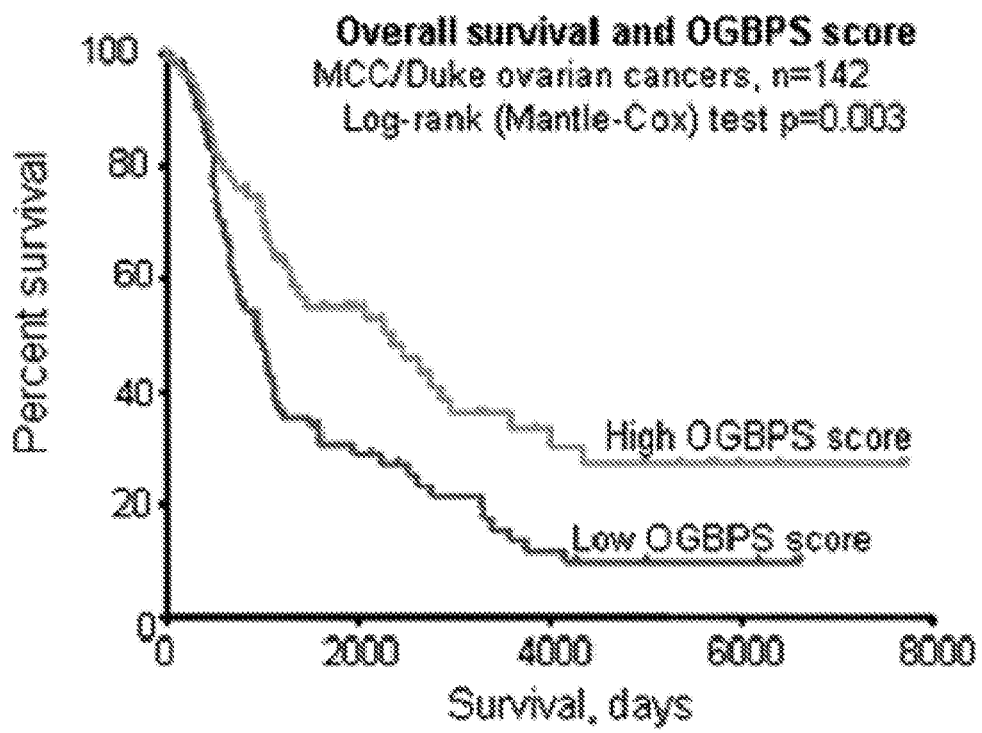
FIGS. 2A to 2D are Kaplan-Meier curves depicting the association between OGBPS PCA score and overall survival from OVCA (FIG. 2A); overall survival and complete response to platinum therapy median cut-off (FIG. 2B); overall survival and incomplete response to platinum therapy (FIG. 2C); and overall survival and cytoreductive status (FIG. 2D). The numbers at risk are shown at the top of graphs. Log-rank test p values indicate significance. CR, complete response; IR, incomplete response; O, optimal; S, suboptimal.
Figure 2B:
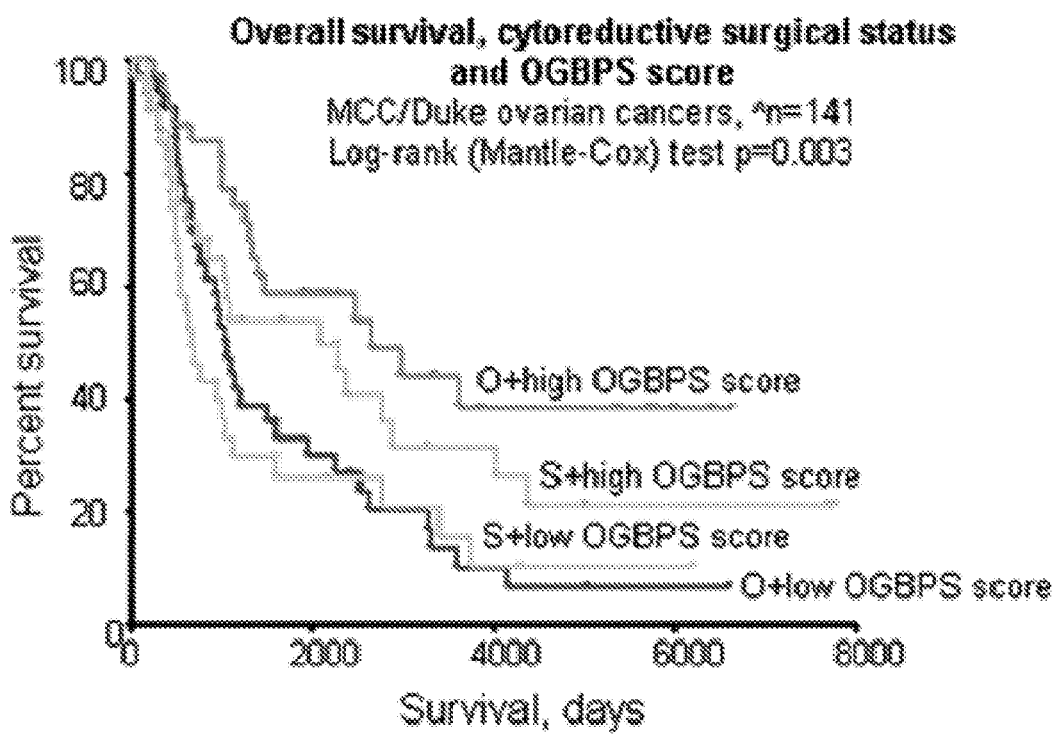
Figure 2C:
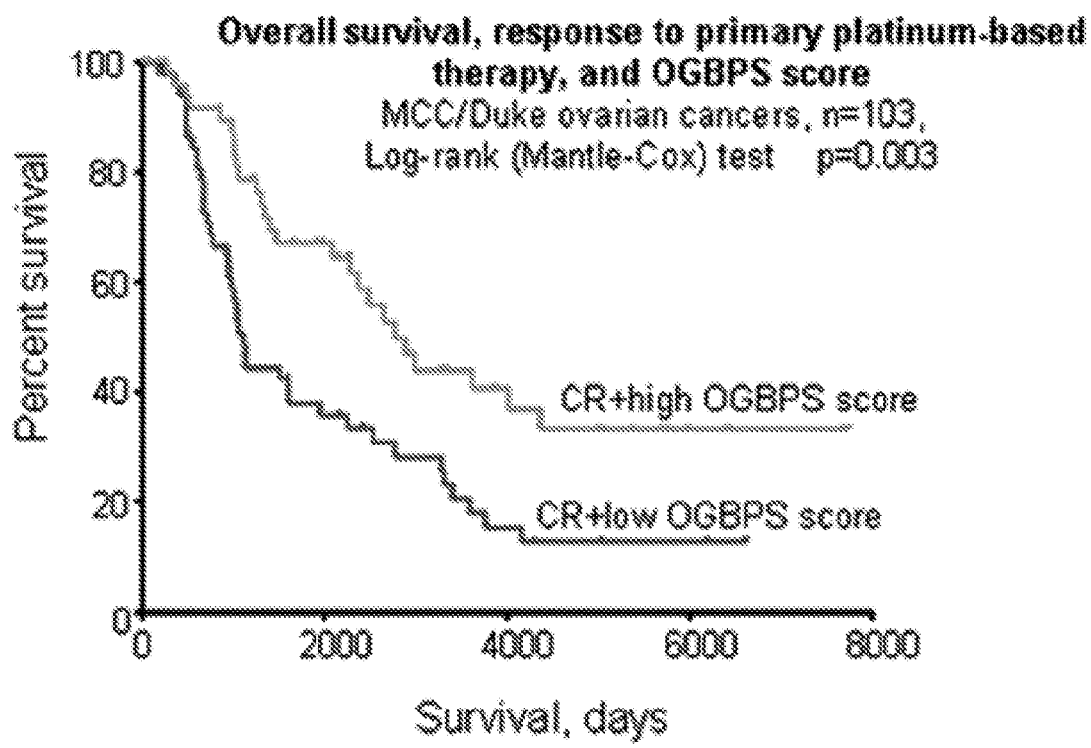
Figure 2D:
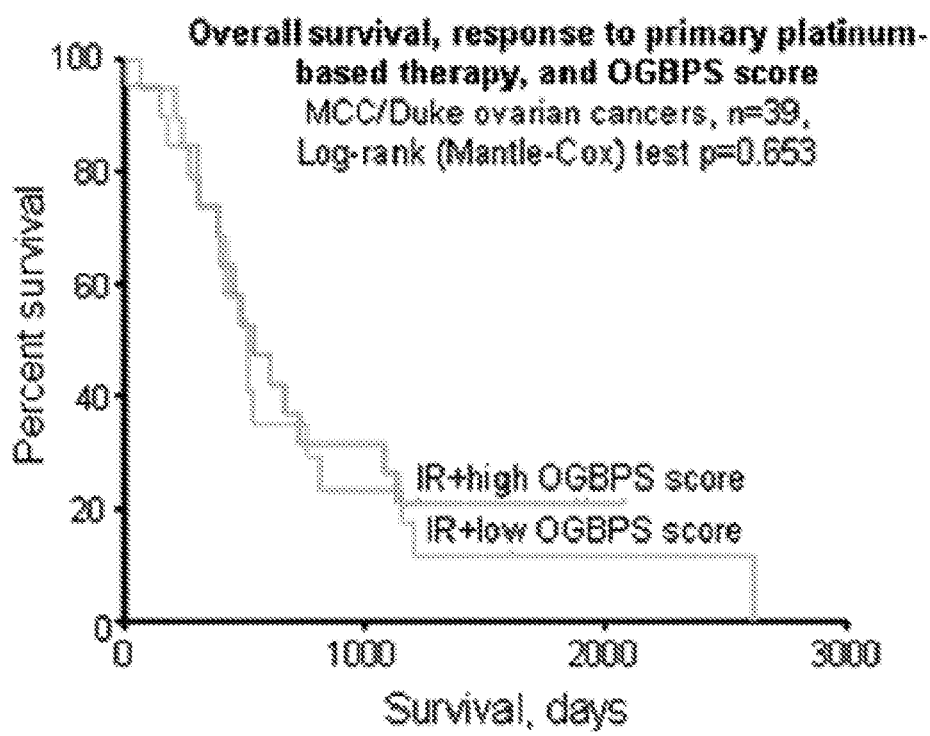

Based on the above findings, PCA was utilized to develop gene expression signature scores for the pathways associated with gemcitabine sensitivity in vitro (Chen D T, et al. Breast Cancer Res Treat 119: 335-46). In this way, a 34-gene "O-glycan biosynthesis pathway signature" (OGBPS) (Table 2) was generated and evaluated in an independent OVCA genomic dataset (Marchion D C, et al. Clin Cancer Res). Using the median value as a threshold to define high versus low OGBPS score, an association between high OGBPS score and favorable survival (p=0.003; FIG. 2A) was identified. A similar association between high OGBPS score and favorable survival was observed in patients who underwent optimal (p=0.002) and suboptimal (approaching significance, p=0.07) cytoreduction (FIG. 2B). Most importantly, OVCA patients with a high OGBPS score who underwent suboptimal cytoreduction had a survival superior to patients with a low OGBPS score who underwent optimal cytoreduction (p=0.003). Interestingly, patients who demonstrated a CR to primary platinum-based therapy but had a high OGBPS score had superior survival compared with those patients who demonstrated a CR but had a low OGBPS score (p=0.003) (FIG. 2C). Patients who had an IR to primary therapy had no difference in survival associated with tumor OGBPS score (p=0.653) (FIG. 2D). When evaluated with cytoreductive status, grade, and age, the OGBPS score was an independent variable associated with survival (p<0.001).

No associations with survival were observed for the first PCA score for the Cell cycle_Role of Nek in cell cycle regulation (59 genes, p=0.3107) or the Immune response_Antiviral actions of Interferons pathway (66 genes, p=0.5411).

Discussion

In this analysis, an in vitro and in vivo genome-wide approach was applied to define the molecular underpinnings of OVCA gemcitabine sensitivity. Genes and molecular signaling pathways associated with OVCA sensitivity to gemcitabine were identified. In addition, the OGBPS associated with in vitro gemcitabine response and also overall survival from OVCA were identified.

Previous efforts to define the molecular basis of gemcitabine resistance have identified molecules such as deoxycytidine kinase (dCK) (Ruiz van Haperen V W, et al. Cancer Res 54: 4138-43, 1994; Galmarini C M, et al. Leukemia 15: 875-90, 2001; Jordheim L, et al. Curr Drug Targets 4: 443-60, 2003; van der Wilt C L, et al. Adv Exp Med Biol 486: 287-90, 2000), ribonucleotide reductase (Cory J G and Sato A. Mol Cell Biochem 53-54: 257-66, 1983; Thelander L and Berg P. Mol Cell Biol 6: 3433-42, 1986; Zhou B S, et al. Clin Exp Metastasis 16: 43-9, 1998), and human equilibrative nucleoside transporter-1 (hENT1) (Mackey J R, et al. Cancer Res 58: 4349-57, 1998; Garcia-Manteiga J, et al. Clin Cancer Res 9: 5000-8, 2003; Mackey J R, et al. J Natl Cancer Inst 91: 1876-81, 1999; Rauchwerger D R, et al. Cancer Res 60: 6075-9, 2000; Ritzel M W, et al. Mol Membr Biol 18: 65-72, 2001). Decreased activity of dCK, which phosphorylates gemcitabine to its monophosphate form, has previously been reported to be associated with resistance to gemcitabine (Ruiz van Haperen V W, et al. Cancer Res 54: 4138-43, 1994; Galmarini C M, et al. Leukemia 15: 875-90, 2001; Jordheim L, et al. Curr Drug Targets 4: 443-60, 2003; van der Wilt C L, et al. Adv Exp Med Biol 486: 287-90, 2000). Consistent with these data, a negative correlation between OVCA cell line mRNA expression of the dCK gene and increasing gemcitabine resistance (Pearson correlation: −0.33, p=0.05) is demonstrated. Previously, overexpression of the M1 and M2 subunits of ribonucleotide reductase (RRM1 and RRM2) has been demonstrated to be associated with gemcitabine resistance in gastrointestinal cancer cells (Davidson J D, et al. Cancer Res 64: 3761-6, 2004; Jung C P, et al. Clin Cancer Res 7: 2527-36, 2001). In the above analysis, no association was observed between gemcitabine resistance and expression of RRM1, although an association between low levels of RRM2 expression (using median expression as a threshold) and high gemcitabine $IC_{50}$ (p<0.02) was observed. It is unclear why these findings are contradictory to those of Davidson et al. (Davidson J D, et al. Cancer Res 64: 3761-6, 2004); however, they may be due to differences in cancer types studied. Inhibition of hENT1 was previously reported to be associated with gemcitabine chemoresistance (Mackey J R, et al. Cancer Res 58: 4349-57, 1998; Rauchwerger D R, et al. Cancer Res 60: 6075-9, 2000). This correlates with the above findings in which a negative correlation between OVCA cell line mRNA expression of the hENT1 gene and increasing gemcitabine resistance (Pearson correlation: −0.3, p=0.06) was demonstrated.

The process of glycosylation involves the enzymatic addition of carbohydrates to proteins or lipids and is the most common form of post-translational modification. Three categories of protein-linked glycans exist, including those linked to the amide group of asparagine (N-linked), those linked to the hydroxyl group of serine, threonine, or hydroxylysine 3 (O-linked), and those linked to a carboxyl group of tryptophan (C-linked) (Hofsteenge J, et al. Biochemistry 33: 13524-30, 1994). The main pathway for complex O-glycan biosynthesis is located in the endoplasmic reticulum and Golgi compartments, restricting glycosylation largely to the endoplasmic reticulum, Golgi, lysosomal, plasma membrane, and secretory proteins, with the exception of nuclear and cytosolic proteins, which can be modified with a single O-linked GlcNAc (Wells L and Hart G W, et al. FEBS Lett 546: 154-8, 2003). O-glycans have been reported to have a broad range of functions in protein structure and stability, immunity, receptor-mediated signaling, nonspecific protein interactions, modulation of the activity of enzymes and signaling molecules, and protein expression and processing (Wells L and Hart G W, et al. FEBS Lett 546: 154-8, 2003; Varki A. Glycobiology 3: 97-130, 1993). Although these biological roles range in importance, they can be critical for development, growth, function, and survival. Moreover, a specific O-glycan may influence a range of functions at different locations and times within an organism (Varki A. Glycobiology 3: 97-130, 1993). Previously, limited access to endoglycosidases to cleave intact O-glycans from their protein backbone, as well as the extreme diversity of their structures, has limited research relative to study of N-linked glycan pathway-linked diseases (historically considered the congenital disorders of glycosylation). More recently, in human cancers, O-glycans have been shown to play important roles in cancer cell attachment, signaling, invasion (Fuster M M, et al. Cancer Res 63: 2775-81, 2003; Gabius H J. Crit Rev Immunol 26: 43-79, 2006; Huet G, et al. Biochimie 85: 323-30, 2003; Ulloa F and Real F X. J Biol Chem 278: 12374-83, 2003), and survival in the bloodstream Inhibition of the O-glycan pathway in colorectal cancer cell lines has been shown to inhibit cell growth and induce apoptosis (Patsos G, et al. Glycobiology 19: 382-98, 2009). More recently, downregulation of the N-glycan biosynthesis pathway was reported to be associated with chemoresistance in cholangiocarcinoma cell lines (Sato J, et al. J Hepatobiliary Pancreat Sci 18: 700-11, 2011).

To date, we are unaware of any reports suggesting that the O-glycan pathway influences OVCA cell response to therapeutic interventions or overall survival. In this study, expression of the O-glycan pathway (quantified by a OGBPS score) was associated with OVCA overall survival when analysis was done for 1) all patients with OVCA, 2) patients who underwent optimal OVCA surgical cytoreduction, and 3) patients who experienced a CR to primary surgery plus platinum-based therapy. The association between OGBPS score and overall survival for patients who underwent suboptimal surgical cytoreduction did not reach statistical significance (p=0.07), and no association was identified in patients who experienced an IR to primary surgery plus platinum-based therapy. When evaluated with cytoreductive status, grade, and age, the OGBPS score was an independent variable associated with survival (p<0.001). The explanation for the associations between OGBPS and OVCA survival is likely complex. Although in this study the O-glycan pathway was identified by its association with in vitro gemcitabine sensitivity, the impact of the pathway on overall survival may not be driven by its effect on gemcitabine sensitivity. In fact, high OGBPS score was associated with resistance to gemcitabine, yet a more favorable outcome for patients with OVCA. As noted above, O-glycans are known to influence cancer cell attachment, signaling, invasion, and survival in the bloodstream (Fuster M M, et al. Cancer Res 63: 2775-81, 2003; Gabius H J. Crit Rev Immunol 26: 43-79, 2006; Huet G, et al. Biochimie 85: 323-30, 2003; Ulloa F and Real F X. J Biol Chem 278: 12374-83, 2003).

TABLE 1

Gemcitabine $IC_{50}$.

| Cell line | $IC_{50}$ (mean) | $IC_{50}$ (SD) | N |
|---|---|---|---|
| A2008 | 163.9E−9 | 309.0E−9 | 12 |
| A2780CP | 366.4E−9 | 696.6E−9 | 9 |
| A2780S | 51.8E−9 | 46.5E−9 | 4 |
| BG1 | 30.4E−6 | 27.6E−6 | 8 |
| C13 | 418.1E−9 | 804.0E−9 | 9 |
| CAOV2 | 3.9E−6 | 8.5E−6 | 12 |
| CAOV3 | 2.2E−9 | 1.2E−9 | 5 |
| CHI | 268.6E−9 | 522.6E−9 | 26 |
| CHIcisR | 23.7E−9 | 58.8E−9 | 13 |
| Dov13 | 6.0E−9 | 3.5E−9 | 4 |
| FUOV1 | 59.4E−6 | 6.9E−6 | 3 |
| HeyA8 | 1.5E−6 | 2.4E−6 | 6 |
| IGR-OV1 | 531.2E−9 | 1.3E−6 | 14 |
| IMCC3 | 942.6E−9 | 1.1E−6 | 15 |
| IMCC5 | 105.1E−9 | 159.6E−9 | 20 |

TABLE 1-continued

Gemcitabine $IC_{50}$.

| Cell line | $IC_{50}$ (mean) | $IC_{50}$ (SD) | N |
|---|---|---|---|
| M41 | 39.5E−9 | 18.7E−9 | 5 |
| M41CSR | 37.4E−9 | 34.4E−9 | 12 |
| MCAS | 56.4E−6 | 99.8E−6 | 8 |
| OV2008 | 383.8E−9 | 1.1E−6 | 15 |
| OV90 | 18.9E−9 | 11.9E−9 | 9 |
| Ovary1847 | 864.6E−9 | 2.7E−6 | 19 |
| OVCA420 | 12.7E−6 | 22.0E−6 | 5 |
| OVCA429 | 22.2E−9 | 24.2E−9 | 5 |
| OVCA432 | 14.9E−6 | 25.7E−6 | 3 |
| OVCA433 | 9.9E−9 | 10.9E−9 | 5 |
| OVCAR10 | 671.9E−9 | 2.5E−6 | 16 |
| OVCAR2 | 22.0E−9 | 30.8E−9 | 17 |
| OVCAR3 | 6.2E−6 | 14.0E−6 | 14 |
| OVCAR4 | 655.3E−9 | 870.8E−9 | 5 |
| OVCAR5 | 278.3E−9 | 721.8E−9 | 17 |
| OVCAR8 | 272.6E−9 | 681.6E−9 | 12 |
| PEO1 | 134.7E−9 | 244.5E−9 | 9 |
| PEO4 | 536.2E−9 | 868.6E−9 | 10 |
| SK-OV-3 | 16.1E−6 | 30.5E−6 | 11 |
| SK-OV-4 | 3.3E−9 | 1.6E−9 | 12 |
| SK-OV-6 | 3.5E−6 | 10.4E−6 | 11 |
| T8 | 255.6E−9 | 456.6E−9 | 9 |
| TOV-112D | 44.5E−6 | 67.3E−6 | 9 |
| TOV-21G | 764.1E−9 | 1.5E−6 | 11 |
| Tyknu | 4.6E−9 | 2.8E−9 | 4 |
| TyknuCisR | 8.5E−9 | 8.4E−9 | 8 |

TABLE 2

OGBPS 34 genes.

| | | |
|---|---|---|
| NM_020981_at | B3GALT1 | Beta-1,3-galactosyltransferase |
| NM_003783_at | B3GALT2 | Beta-1,3-galactosyltransferase, beta-3-galt2 |
| NM_003782_a_at | B3GALT4 | Beta-1,3-galactosyltransferase 4 |
| NM_033171_at | B3GALT5 | GlcNAc-beta-1,3-galactosyltransferase 5, GLCT5, homolog of C |
| NM_138706_at | B3GNT6 | Beta-1,3-N-acetylglucosaminyltransferase protein |
| U10474_at | B4GALT1 | B4GALT1 |
| NM_003780_at | B4GALT2 | B4GALT2 |
| NM_003779_at | B4GALT3 | Beta4Gal-T3 |
| NM_020156_at | C1GALT1 | Core 1 synthase, glycoprotein-N-acetylgalactosamine |
| AW798875_at | GALNT1 | Polypeptide N-acetylgalactosaminyltransferase 1 |
| NM_024564_at | GALNT10 | Polypeptide N-acetylgalactosaminyltransferase 10 |
| NM_022087_at | GALNT11 | Polypeptide N-acetylgalactosaminyltransferase 11 |
| AI638649_at | GALNT12 | Polypeptide N-acetylgalactosaminyltransferase 12 |
| AK131195_a_at | GALNT13 | UDP-N-acetyl-alpha-D-galactosamine:polypeptide |
| NM_024572_s_at | GALNT14 | Polypeptide N-acetylgalactosaminyltransferase 14 |
| AK097996_at | GALNT2 | Polypeptide N-acetylgalactosaminyltransferase 2 |
| BX647473_a_at | GALNT3 | Polypeptide N-acetylgalactosaminyltransferase 3 |
| NM_003774_at | GALNT4 | Polypeptide N-acetylgalactosaminyltransferase 4 |
| BX097451_s_at | GALNT5 | Polypeptide N-acetylgalactosaminyltransferase 5 |
| BU542820_at | GALNT6 | Polypeptide N-acetylgalactosaminyltransferase 6 |
| NM_017423_at | GALNT7 | Polypeptide N-acetylgalactosaminyltransferase 7 |
| BM719843_a_at | GALNT8 | N-acetylgalactosaminyltransferase 8 |
| NM_021808_at | GALNT9 | Polypeptide N-acetylgalactosaminyltransferase 9 |
| NM_020692_at | GALNTL1 | Polypeptide N-acetylgalactosaminyltransferase 16 |
| BC030625_at | GALNTL2 | Polypeptide N-acetylgalactosaminyltransferase 13 |
| NM_198516_at | GALNTL4 | UDP-N-acetyl-alpha-D-galactosamine |
| NM_145292_at | GALNTL5 | UDP-N-acetyl-alpha-D-galactosamine |
| NM_001490_at | GCNT1 | Beta-1,6-N-acetylglucosaminyltransferase 1 |
| NM_145649_s_at | GCNT2 | Beta-1,6-N-acetylglucosaminyltransferase 2 |
| NM_004751_at | GCNT3 | Beta1,6-N-acetylglucosaminyltransferase 3 |
| CR619813_at | ST3GAL1 | 3-Sialyltransferase,Gal-NAc6S |
| AK127322_at | ST3GAL2 | Beta-galactoside alpha-2,3-sialytransferase |
| NM_018414_at | ST6GALN | 6-Sialyltransferase I alpha-N-acetylgalactosaminide alpha-2 |
| BC067524_a_at | WBSCR17 | Polypeptide N-acetylgalactosaminyltransferase, Williams-Beuren syndrome chromosome region 17 |

TABLE 3

Genes associated with in vitro gemcitabine chemoresistance

| Probe Set ID | Gene Name | Gene Description | Score | P-value |
| --- | --- | --- | --- | --- |
| ENST00000376242_at | PSORS1C3 | PSORS1C3, AB023059.1 | 0.785 | 1.22E−09 |
| AK123047_a_at | NR3C2 | NR3C2, MGC133092, MLR, MR, MCR | 0.749 | 1.72E−08 |
| ENST00000366558_a_at | KMO | KMO, dJ317G22.1 | 0.728 | 6.82E−08 |
| NM_152772_at | TCP11L2 | t-complex 11 (mouse) like 2 | 0.700 | 3.61E−07 |
| NM_003890_at | FCGBP | Human IgG Fc binding protein | 0.688 | 6.62E−07 |
| NM_021936_at | PAPPA2 | pregnancy-associated plasma preproprotein-A2 | 0.680 | 9.89E−07 |
| NM_139173_s_at | NHEDC1 | Na+/H+ exchanger domain CG10806-like | 0.676 | 1.25E−06 |
| NM_152888_s_at | COL22A1 | collagen, type XXII, alpha 1 | 0.656 | 3.29E−06 |
| NM_016242_at | EMCN | endomucin, endomucin-2 | 0.654 | 3.60E−06 |
| AL133118_at | MAPKSP1 | MAPKSP1, MAPBP, MP1, MAP2K1IP1 | 0.638 | 7.26E−06 |
| NM_030923_s_at | TMEM163 | transmembrane protein 163 | 0.636 | 8.00E−06 |
| NM_024013_at | IFNA1 | IFNA1, IFL, IFN, IFN-α, IFNA13, IFN α-D, LeIF D | 0.631 | 9.60E−06 |
| NM_199235_at | COLEC11 | collectin sub-family member 11 | 0.626 | 1.18E−05 |
| NM_003585_at | DOC2B | double C2-like domains, β | 0.620 | 1.55E−05 |
| NM_005472_at | KCNE3 | cardiac voltage-gated K channel accessory | 0.618 | 1.65E−05 |
| NM_194309_at | C21orf125 | C21orf125, PRED49, FLJ38036 | 0.618 | 1.67E−05 |
| ENST00000260323_at | UNC13C | unc-13 homolog C | 0.616 | 1.82E−05 |
| ENST00000234725_at | TMEM48 | transmembrane protein 48 | −0.612 | 2.09E−05 |
| NM_198058_at | ZNF266 | zinc finger protein 266 | −0.603 | 3.06E−05 |
| AW510703_at | SLC15A4 | solute carrier family 15, member 4 | 0.601 | 3.20E−05 |
| NM_020119_at | ZC3HAV1 | zinc finger antiviral protein | −0.597 | 3.76E−05 |
| NM_019104_s_at | LIN37 | lin-37 homolog | 0.596 | 3.91E−05 |
| NM_022774_at | DEM1 | DEM1, FLJ11445, FLJ13183, FLJ21144, C1orf176 | −0.596 | 3.92E−05 |
| AA723953_at | SGCD | Sarcoglycan, delta (35 kD dystrophin-associated glycan) | 0.591 | 4.82E−05 |
| NM_012253_s_at | TKTL1 | Transketolase-like 1 | 0.590 | 4.87E−05 |
| NM_175613_a_at | CNTN4 | Axonal cell adhesion molecule contactin 4 | 0.590 | 4.97E−05 |
| NM_006198_at | PCP4 | Purkinje cell protein 4 | 0.589 | 5.01E−05 |
| NM_012391_at | SPDEF | Human prostate specific Ets, PDEF | 0.588 | 5.25E−05 |
| AK124251_at | LHFPL3 | LHFP-like protein 3 | 0.586 | 5.65E−05 |
| AK024279_a_at | WIPI2 | WD repeat domain, phosphoinositide interacting 2 | −0.583 | 6.38E−05 |
| N25888_a_at | GDF15 | Growth differentiation factor 15 | 0.581 | 6.72E−05 |
| NM_000705_at | ATP4B | ATPase, H+/K+ transporting, beta polypeptide | 0.578 | 7.57E−05 |
| AK097996_at | GALNT2 | Polypeptide N-acetylgalactosaminyltransferase 2 | −0.577 | 7.71E−05 |
| NM_014848_at | SV2B | Synaptic vesicle protein 2B | 0.577 | 7.96E−05 |
| AL049464_at | THSD4 | Thrombospondin, type I, domain containing 4 | 0.576 | 8.03E−05 |
| BM668558_at | SART1 | Squamous cell carcinoma antigen recognized by T c | −0.576 | 8.23E−05 |
| CR606639_a_at | ZFP57 | Zinc finger protein 57 | 0.574 | 8.62E−05 |
| NM_018053_at | XKR8 | X Kell blood group precursor-related family | −0.574 | 8.73E−05 |
| NM_002239_at | KCNJ3 | Subfamily, potassium inwardly-rectifying channel J3 | 0.573 | 9.09E−05 |
| BC009808_at | NBR1 | Neighbor of BRCA1 gene 1 protein | 0.573 | 9.18E−05 |
| ENST00000360944_s_at | RBAK | RB-associated KRAB repressor | −0.572 | 9.19E−05 |
| AK023318_s_at | CBARA1 | Calcium binding atopy-related autoantigen 1 | 0.570 | 9.94E−05 |
| BQ574912_s_at | TOMM5 | TOMM5, C9orf105, RP11-263I4.1, Tom5, bA613M10.3 | −0.565 | 0.0001177 |
| ENST00000361262_at | SMC5 | Structural maintenance of chromosomes 5 | −0.563 | 0.0001256 |
| ENST00000369578_a_at | ZNF292 | Zinc-finger domain protein | 0.563 | 0.000126 |
| BC050372_a_at | OLAH | Oleoyl-ACP hydrolase | 0.563 | 0.0001284 |
| NM_172238_at | TFAP2D | Transcription factor AP-2 beta | 0.563 | 0.0001288 |
| NM_134266_at | SLC26A7 | Solute carrier family 26, member 7 | 0.562 | 0.0001305 |
| BC027487_at | C15orf62 |  | 0.561 | 0.0001364 |
| DC311076_a_at | PIP4K2A | Phosphatidylinositol-4-phosphate 5-kinase type-2 | 0.561 | 0.0001374 |
| NM_006786_at | UTS2 | Human Urotensin II | 0.559 | 0.0001448 |
| BC036592_at | GABRB2 | Gamma-aminobutyric-acid receptor beta-2 subuni | 0.557 | 0.0001555 |
| NM_018667_at | SMPD3 | Sphingomyelin phosphodiesterase 3 | 0.554 | 0.0001718 |
| NM_014717_at | ZNF536 | zinc finger protein 536 | 0.552 | 0.000184 |

TABLE 3-continued

Genes associated with in vitro gemcitabine chemoresistance

| Probe Set ID | Gene Name | Gene Description | Score | P-value |
| --- | --- | --- | --- | --- |
| NM_014629_s_at | ARHGEF10 | Rho guanine nucleotide exchange factor 10 | −0.552 | 0.000185 |
| NM_001005212_at | OR9Q1 | Olfactory receptor, family 9, subfamily Q | −0.552 | 0.0001851 |
| CR603904_s_at | EIF2AK2 | Protein kinase RNA-regulated, (EIF2AK1) | −0.550 | 0.0001982 |
| BC050525_at | USP1 | Ubiquitin specific processing protease 1 | −0.549 | 0.0002021 |
| AK024011_at | TOE1 | Target of EGR1 | −0.547 | 0.0002146 |
| NM_001037165_s_at | FOXK1 | Forkhead box K1 | −0.547 | 0.0002163 |
| DW432944_at | C4orf36 | C4orf36, hypothetical protein LOC132989, MGC26744, Hs.507712 | 0.547 | 0.0002164 |
| NM_001551_at | IGBP1 | Immunoglobulin-binding protein 1 | 0.546 | 0.0002189 |
| BX091412_at | KLHL34 | KLHL34, kelch-like 34, MGC125650, RP11-450P7.3, FLJ34960 | −0.546 | 0.0002246 |
| R37641_at | CA10 | Carbonic anhydrase-related protein 10 | 0.545 | 0.0002306 |
| NM_000343_at | SLC5A1 | Human Na+/glucose cotransporter 1 mRNA | 0.545 | 0.0002323 |
| BG776661_at | C10orf104 | C10orf104, FLJ33728 | 0.543 | 0.0002473 |
| BC122561_at | LIN7A | Lin-7 homolog A | 0.542 | 0.0002521 |
| NM_016486_at | TMEM69 | Transmembrane protein 69 | −0.541 | 0.0002638 |
| M18414_at | TRDV1 | TRDV1, hDV101S1 | 0.541 | 0.000264 |
| NM_014503_at | UTP20 | UTP20, down-regulated in metastasis | −0.539 | 0.0002797 |
| AY153484_at | PAX2 | Paired box gene 2 | 0.537 | 0.0002962 |
| BU589560_at | CLDN12 | CLDN12, claudin 12 | 0.536 | 0.0003033 |
| NM_001422_s_at | ELF5 | ELF5, ESE2, ESE-2 | 0.536 | 0.0003043 |
| BC038514_a_at | DPP10 | Dipeptidyl peptidase 10 | 0.536 | 0.0003078 |
| BX649183_at | IVNS1ABP | Influenza virus NS1A binding protein | 0.531 | 0.0003515 |
| NM_032588_at | TRIM63 | Muscle specific ring finger protein 1 | 0.531 | 0.0003543 |
| NM_153705_at | KDELC2 | KDELC2, MGC33424, KDEL (Lys-Asp-Glu-Leu) containing 2 | −0.531 | 0.0003585 |
| BX647977_a_at | RNMT | Human RNA (guanine-7-) methyltransferase | 0.530 | 0.0003622 |
| NM_032525_at | TUBB6 | Tubulin beta-6 chain | −0.530 | 0.0003656 |
| NM_017983_at | WIPI1 | Human WD-repeat protein Interacting with PhosphoI | 0.530 | 0.0003692 |
| NM_003101_at | SOAT1 | Sterol O-acyltransferase 1 | −0.530 | 0.0003695 |
| NM_182538_at | SPNS3 | SPNS3, spinster homolog 3, MGC29671 | 0.529 | 0.0003766 |
| BU730580_at | RHO | Rhodopsin | 0.528 | 0.0003879 |
| AL713688_s_at | hCG_2009921 | hCG_2009921, LOC441204 | 0.527 | 0.0003942 |
| NM_016426_at | GTSE1 | GTSE1, G-2 and S-phase expressed 1 | −0.526 | 0.000407 |
| DB377031_x_at | PSG4 | Pregnancy specific beta-1-glycoprotein 4 | 0.526 | 0.0004144 |
| BC101614_a_at | WDR72 | WD repeat domain 72 | 0.523 | 0.0004451 |
| BI761936_a_at | C12orf69 | | 0.522 | 0.0004594 |
| NM_021808_at | GALNT9 | Polypeptide N-acetylgalactosaminyltransferase 9 | 0.521 | 0.0004817 |
| NM_022127_at | SLC28A3 | Concentrative Na+-nucleoside cotransporter | 0.520 | 0.00049 |
| AK098151_at | PDK4 | Pyruvate dehydrogenase kinase 4 | 0.519 | 0.0005028 |
| NM_174900_at | ZFP42 | Zinc finger protein 42 | 0.519 | 0.0005127 |
| BC035128_a_at | MXI1 | MAX interacting protein 1 | 0.519 | 0.0005142 |
| NM_001085_at | SERPINA3 | Serine proteinase inhibitor, clade A, member 3 | 0.516 | 0.0005467 |
| AL564246_at | ZNF277 | Zinc finger protein 277 | 0.516 | 0.0005478 |
| NM_002813_at | PSMD9 | Proteasome 26S non-ATPase subunit 9 | −0.515 | 0.0005733 |
| NM_005318_at | H1F0 | H1 histone family, member 0 | −0.515 | 0.0005758 |
| AL136587_at | AGPAT5 | 1-acylglycerol-3-phosphate O-acyltransferase 5 | −0.514 | 0.0005852 |
| NM_015474_at | SAMHD1 | SAM domain- and HD domain-containing protein 1 | −0.514 | 0.0005942 |
| AV708719_at | FAM65C | FAM65C, dJ530I15.2, FLJ00360, FLJ32230, C20orf175 | 0.513 | 0.0006068 |
| AF313619_at | PAQR8 | Lysosomal membrane protein in brain 1 | 0.513 | 0.0006086 |
| NM_005656_at | TMPRSS2 | Transmembrane protease, serine 2 catalytic chain | 0.513 | 0.0006113 |

TABLE 3-continued

Genes associated with in vitro gemcitabine chemoresistance

| Probe Set ID | Gene Name | Gene Description | Score | P-value |
|---|---|---|---|---|
| CN310658_s_at | FXYD6 | FXYD domain-containing ion transport regulator 6 | 0.512 | 0.000615 |
| NM_032609_s_at | COX4I2 | Cytochrome c oxidase subunit 4 isoform 2 | 0.509 | 0.0006842 |
| NM_007168_at | ABCA8 | ATP-binding cassette, sub-family A member 8 | 0.507 | 0.00071 |
| NM_012478_at | WBP2 | WW domain binding protein 2 | 0.507 | 0.0007162 |
| AK125857_at | NUP62 | Nuclear pore glycoprotein p62 | −0.507 | 0.0007163 |
| NM_000078_at | CETP | Cholesteryl Ester Transfer Protein | 0.507 | 0.0007259 |
| NM_001102610_a_at | TUBGCP5 | tubulin, gamma complex associated protein 5 | −0.505 | 0.0007604 |
| NM_005773_at | ZNF256 | Zinc finger protein 256 | −0.505 | 0.0007613 |
| CB852298_at | CHORDC1 | Chord domain-containing protein 1 | −0.505 | 0.0007663 |
| NM_024306_at | FA2H | Fatty acid hydroxylase domain containing 1 | 0.504 | 0.0007716 |
| NM_031891_a_at | CDH20 | Cadherin 20 | 0.503 | 0.000811 |
| NM_020380_at | CASC5 | Cancer susceptibility candidate 5 | −0.502 | 0.0008354 |
| NM_003417_at | ZNF264 | Zinc finger protein 264 | −0.501 | 0.000841 |
| NM_018840_at | C20orf24 | C20orf24, PNAS-11, RAB5-interacting protein, RIP5 | −0.501 | 0.0008587 |
| NM_021269_s_at | ZNF708 | Zinc finger protein 15-like 1 (KOX 8) | −0.500 | 0.0008837 |
| NM_020167_at | NMUR2 | Neuromedin U receptor 2 | 0.499 | 0.0008887 |
| NM_001112724_at | STK32A | Serine/threonine kinase 32A | 0.499 | 0.0008995 |
| AK075129_s_at | RHOBTB1 | Rho-related BTB domain containing 1 | 0.498 | 0.0009097 |
| ENST00000357899_a_at | ZBTB44 | Zinc finger and BTB domain containing 44 | 0.498 | 0.0009199 |
| CR456455_s_at | SERHL | Serine hydrolase-like | −0.498 | 0.0009238 |
| NM_080717_at | TBX5 | T-box transcription factor TBX5 | 0.498 | 0.0009268 |
| BC098116_at | ABCA11P | FLJ14297, MGC120309, MGC120310, MGC120312, MGC132744, MGC138274 | −0.498 | 0.0009313 |
| AK026107_a_at | RBM25 | RNA binding motif protein 25, RNA-binding motif protein 25 | −0.497 | 0.0009449 |
| LIT1500_s_at | NOL5A | Nucleolar protein 5A | −0.497 | 0.0009486 |
| AF233261_a_at | OTOR | OTOR, fibrocyte-derived protein, Melanoma Inhibitory Activity-Likebprotein | 0.497 | 0.0009601 |
| CR610033_a_at | TOM1L1 | Target of Myb-like protein 1 | 0.496 | 0.0009693 |
| AI144436_at | SF3A3 | Spliceosome associated protein 61, Splicing factor 3A subunit 3 | −0.495 | 0.0009879 |
| AB053232_at | GAL3ST3 | Galactose 3'-sulfotransferase, galactose-3-O-sulfotransferase 3 | 0.495 | 0.0009897 |
| NM_206915_s_at | NGFRAP1 | NGFRAP1, BEX3, DXS6984E, HGR74, NADE, Bex | −0.495 | 0.0009941 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining the prognosis of a patient with ovarian cancer, comprising
    a) assaying a biological sample from the subject for the expression level of at least ten (10) O-glycan biosynthesis pathway (OGBP) genes selected from the group consisting of B3GALT1, B3GALT2, B3GALT4, B3GALT5, B3GNT6, B4GALT1, B4GALT2, B4GALT3, C1GALT1, GALNT1, GALNT10, GALNT11, GALNT12, GALNT13, GALNT14, GALNT2, GALNT3, GALNT4, GALNT5, GALNT6, GALNT7, GALNT8, GALNT9, GALNTL1, GALNTL2, GALNTL4, GALNTL5, GCNT1, GCNT2, GCNT3, ST3GAL1, ST3GAL2, ST6GALN, and WBSCR17;
    b) comparing the expression levels of the genes to control values to produce a gene profile; and
    c) analyzing the gene profile to calculate an OGBP risk score using standard statistical analysis, and
    d) optimally debulking the ovarian cancer if the patient has a high OGBP score, and not debulking or only suboptimally debulking the ovarian cancer if the patient has a low OGBP score.

2. The method of claim 1, wherein a favorable prognosis comprises an increased likelihood of survival after treatment with primary chemotherapy.

3. The method of claim 1, further comprising treating the patient with chemotherapy if the patient has a high OGBP score.

4. The method of claim 1, wherein step a) comprises assaying the biological sample from the subject for the expression level of a panel of OGBP genes comprising B3GALT1, B3GALT2, B3GALT4, B3GALT5, B3GNT6, B4GALT1, B4GALT2, B4GALT3, C1GALT1, GALNT1, GALNT10, GALNT11, GALNT12, GALNT13, GALNT14, GALNT2, GALNT3, GALNT4, GALNT5, GALNT6, GALNT7, GALNT8, GALNT9, GALNTL1, GALNTL2, GALNTL4, GALNTL5, GCNT1, GCNT2, GCNT3, ST3GAL1, ST3GAL2, ST6GALN, and WBSCR17.

5. The method of claim 2, wherein the chemotherapy comprises gemcitabine.

6. The method of claim 1, wherein the biological sample is assayed for RNA or cDNA levels of the OGBP genes.

7. The method of claim 1, wherein the gene profile is analyzed by multivariate regression analysis or principal component analysis to calculate the OGBP score.

8. The method of claim 1, wherein the ovarian cancer is a surface epithelial-stromal tumor (ovarian adenocarcinoma).

9. The method of claim 1, wherein the biological sample is a tumor biopsy.

* * * * *